United States Patent [19]

Summ

[11] Patent Number: 5,213,100
[45] Date of Patent: May 25, 1993

[54] X-RAY MAMMOGRAPHY APPARATUS WITH A STEREOTACTIC BIOPSY UNIT

[75] Inventor: Herbert Summ, Wilhelmsdorf, Fed. Rep. of Germany

[73] Assignee: Siemens Aktiengesellschaft, Munich, Fed. Rep. of Germany

[21] Appl. No.: 773,538

[22] Filed: Oct. 9, 1991

[30] Foreign Application Priority Data

Dec. 12, 1990 [DE] Fed. Rep. of Germany ... 9016810[U]

[51] Int. Cl.⁵ ............................................. A61B 19/10
[52] U.S. Cl. .................... 128/653.1; 378/37; 606/130
[58] Field of Search ............... 128/653.1, 754, 662.05; 378/37, 196; 606/130, 185; 604/164, 264

[56] References Cited

U.S. PATENT DOCUMENTS

| | | | |
|---|---|---|---|
| 4,576,175 | 3/1986 | Epstein | 128/662.05 |
| 4,784,134 | 11/1988 | Arana . | |
| 4,883,053 | 11/1989 | Simon | 606/130 |
| 4,898,178 | 2/1990 | Wedel | 128/662.05 |
| 5,006,122 | 4/1991 | Wyatt et al. | 606/130 |
| 5,100,411 | 3/1992 | Koutrouvelis | 606/130 |
| 5,116,345 | 5/1992 | Jewell et al. | 606/130 |

FOREIGN PATENT DOCUMENTS

| | | |
|---|---|---|
| 2501436 | 7/1976 | Fed. Rep. of Germany . |
| 3406596 | 9/1985 | Fed. Rep. of Germany . |
| 2584601 | 1/1987 | France ............. 128/754 |

OTHER PUBLICATIONS

"Zusatz zur Bedienungsanleitung" (Supplement to User's Manual) for MAMMOMAT 2 Stereotactic Biopsy Apparatus (Siemens), Apr. 1989.

*Primary Examiner*—Ruth S. Smith
*Assistant Examiner*—Krista M. Pfaffle
*Attorney, Agent, or Firm*—Hill, Steadman & Simpson

[57] ABSTRACT

An x-ray mammography apparatus has a stereotactic biopsy unit having two holders for a biopsy needle, the holders extending parallel to the exposure plane. The free ends of the holders, in which the needle is retained, each have a releasable closure for the needle, so that the biopsy needle can be detached from the holder while remaining inserted in the breast. This permits the patient to be moved away from the mammography apparatus, for example into an operating room, with the needle remaining in place as a means for identifying the location for surgery.

3 Claims, 2 Drawing Sheets

X-RAY MAMMOGRAPHY APPARATUS WITH A STEREOTACTIC BIOPSY UNIT

BACKGROUND OF THE INVENTION

1. Field of the Invention

The present invention is directed to an x-ray mammography apparatus, and in particular to such an apparatus having a stereotactic biopsy unit including two holders for a biopsy needle which extend parallel to the exposure plane.

2. Description of the Prior Art

It is known to combine structures for holding or guiding a biopsy needle with a mammography xray apparatus so that in addition to enabling the production of x-ray exposures, tissue samples can be taken from the breast at an appropriate location. Arrangements which provide for positioning and axial movement of the biopsy needle are known as stereotactic biopsy units.

A stereotactic biopsy unit in combination with an x-ray mammography apparatus is known wherein the stereotactic biopsy unit has two holders for the biopsy needle which extend parallel to the exposure plane of the mammography apparatus. The needle is introduced through the two holders into the breast in an axial direction, and is subsequently withdrawn from both holders in the opposite axial direction with the tissue specimen. While the needle is in the breast, it is not possible for the patient to move away from the apparatus.

SUMMARY OF THE INVENTION

It is an object of the present invention to provide an x-ray mammography apparatus combined with a stereotactic biopsy unit which permits the patient to be moved away from the apparatus, such as for surgery, with the biopsy needle remaining in the breast.

The above object is achieved in accordance with the principles of the present invention in an x-ray mammography apparatus having stereotactic biopsy unit holders for the biopsy needle extending parallel to the exposure plane of the mammography apparatus, wherein the respective free ends of the holders have a releasable closure for holding the biopsy needle. When opened, the releasable closure permits the biopsy needle to be removed from each of the holders without axial displacement of the biopsy needle relative to the breast, such as in a horizontal direction parallel to the exposure plane. After the closures have been opened, the patient, with the biopsy needle remaining in the breast, can be moved away from the x-ray apparatus, for example to an operating room, with the location for the surgery being easily locatable by the presence of the needle.

DESCRIPTION OF THE PREFERRED EMBODIMENTS

Figure 1:
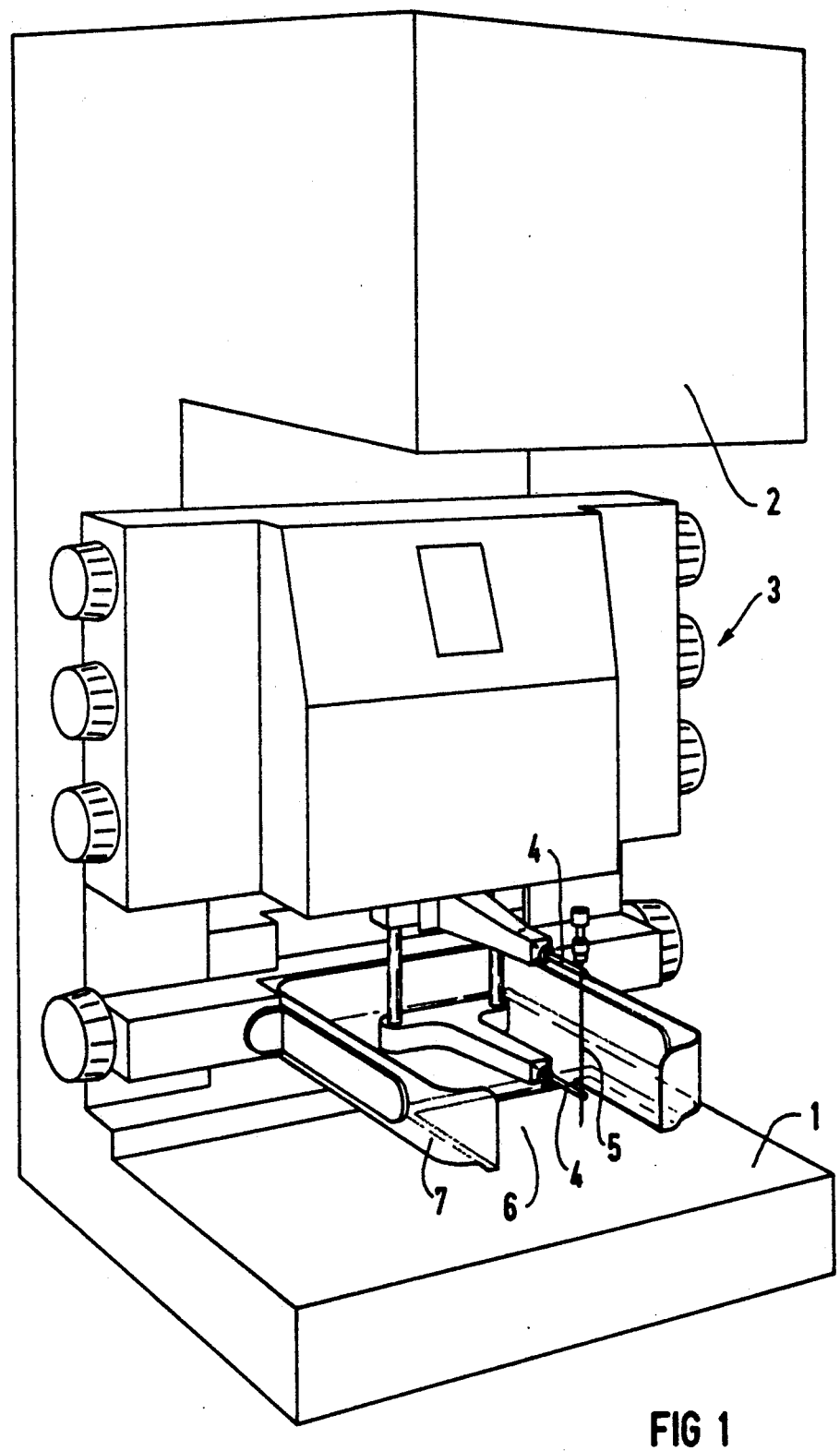
FIG. 1 is a perspective view of an x-ray a mammography apparatus with a stereotactic biopsy unit constructed in accordance with the principles of the present invention.

An x-ray mammography apparatus is shown in FIG. 1 having a seating plate 1, an x-ray radiator 2 and a stereotactic biopsy unit 3. The biopsy unit 3 has two holders 4 for a biopsy needle 5. The biopsy needle 5 is inserted into the holders 4 in the axial direction of the needle 5. The mammography unit includes a compression plate 7 which compresses the breast under examination, and the compression plate 7 has an opening 6 through which the biopsy needle 5 can be inserted.

In accordance with the principles of the present invention, the holders 4 of the biopsy unit 3 each have releasable closure at their respective free ends. When closed, the releasable closure permits the biopsy needle 5 to be introduced and withdrawn from the holders 4 along its axial direction. When opened, the releasable closures permit the biopsy needle 5 to be moved away from the holders 4 in a direction parallel to the exposure plane of the mammography apparatus, i.e., away from the front of the apparatus. This permits the patient to be moved away from the x-ray apparatus with the biopsy needle 5 remaining in the breast.

Figure 2:
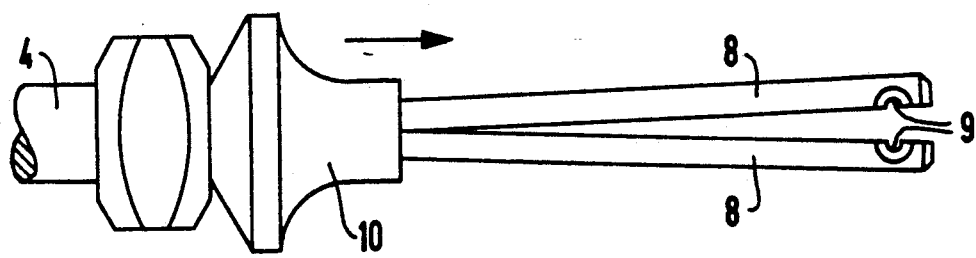
FIGS. 2, 3 and 4 are plan views of a holder for use in the apparatus of FIG. 1 respectively showing three embodiments for a releasable closure for the biopsy needle.
Figure 3:
Figure 4:
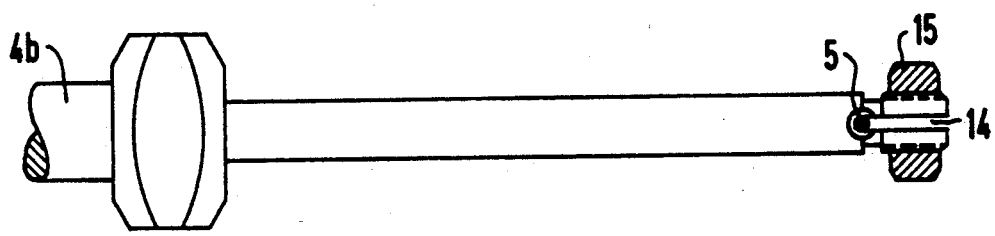

Various embodiment of such a releasable closure are respectively shown in FIGS. 2, 3 and 4. In each figure, only one holder is shown, however, it will be understood that both holders 4 will embody such a releasable closure.

In the embodiment of FIG. 2, the holder 4 has a separable free end, formed by two resilient halves 8, each having a semi-circular recess 9 for receiving the biopsy needle. The halves 8 can be pressed together by sliding a clamping element 10 over the halves 8 in the direction of the arrow, so as to hold the biopsy needle 5 firmly within the recesses 9. For releasing the biopsy needle 5, the clamping element 10 is moved to the position shown in FIG. 2, so that the biopsy needle 5 can be removed from the holders 4.

In the embodiment of FIG. 3, each holder 4a has a cut or channel 11 at its free end, which receives the biopsy needle 5. The biopsy needle 5 can be locked in the channel 11 by a pivotable clip 12 which has a recess 13 which tightly clamps around the biopsy needle 5.

In the embodiment of FIG. 4, each older 4b has a free end provided with a channel or cut 14, which receives the biopsy needle 5. The exterior of the holder 4b substantially coextensive with the channel 14 is threaded. After a biopsy needle 5 has been inserted through the channel 14, the needle 5 is tightly clamped in place by tightening a nut 15 over the threads.

Although modifications and changes may be suggested by those skilled in the art, it is the intention of the inventor to embody within the patent warranted hereon all changes and modifications as reasonably and properly come within the scope of his contribution to the art.

I claim as my invention:

1. In an x-ray mammography apparatus having a stereotactic biopsy unit attached thereto having two holders for a biopsy needle extending parallel to an exposure plane for x-ray exposures, each holder having a free end, wherein the improvement comprises releasable closure means for receiving said biopsy needle and being openable so that said biopsy needle can be detached from said holders and moved away from said holders without axial displacement of said biopsy needle, said releasable closure means comprising:

two resilient halves forming the respective free ends of each of said holders, said halves having respective recesses in registry forming a receptacle for said biopsy needle; and a clamping element slidable along said halves having a first position permitting said receptacle to open, and a second position forcing said halves together to close said receptacle.

2. In an x-ray mammography apparatus having a stereotactic biopsy unit attached thereto having two holders for a biopsy needle extending parallel to an exposure plane for xray exposures, each holder having a free end, wherein the improvement comprises releasable closure means for receiving said biopsy needle and being openable so that said biopsy needle can be detached from said holders and moved away from said holders without axial displacement of said biopsy needle, said releasable closure means having a channel at the respective free ends of said holders for receiving said biopsy needle; and a clip pivotably attached to each of said holders, each said clip having a receptacle at an end thereof movable into a position overlapping said channel in said respective free ends of said holders to retain said biopsy needle.

3. In an x-ray mammography apparatus having a stereotactic biopsy unit attached thereto having two holders for a biopsy needle extending parallel to an exposure plane for x-ray exposures, each holder having a free end, wherein the improvement comprises releasable closure means for receiving said biopsy needle and being openable so that said biopsy needle can be detached from said holders and moved away from said holders without axial displacement of said biopsy needle, said releasable closure means having a channel in the respective free ends of said holders for receiving said biopsy needle, and said releasable closure means having exterior threads substantially coextensive with said channel; and said closure means further including a nut received on said threads thereof which is tightenable to retain said biopsy needle in the channels.

* * * * *